United States Patent
Ledoux et al.

(10) Patent No.: US 10,799,220 B2
(45) Date of Patent: Oct. 13, 2020

(54) ACTIVE DISTRIBUTION OF HIGH-VOLTAGE POWER FOR ULTRASOUND TRANSDUCERS

(71) Applicant: KONINKLIJKE PHILIPS N.V., Eindhoven (NL)

(72) Inventors: Nik Ledoux, Andover, MA (US); Bernard Joseph Savord, Andover, MA (US); Michael Carl Bradshaw, II, Medford, MA (US)

(73) Assignee: Koninklijke Philips N.V., Eindhoven (NL)

( * ) Notice: Subject to any disclaimer, the term of this patent is extended or adjusted under 35 U.S.C. 154(b) by 205 days.

(21) Appl. No.: 15/768,989

(22) PCT Filed: Nov. 2, 2016

(86) PCT No.: PCT/IB2016/056582
§ 371 (c)(1),
(2) Date: Apr. 17, 2018

(87) PCT Pub. No.: WO2017/077456
PCT Pub. Date: May 11, 2017

(65) Prior Publication Data
US 2018/0289361 A1    Oct. 11, 2018

Related U.S. Application Data

(60) Provisional application No. 62/249,416, filed on Nov. 2, 2015.

(51) Int. Cl.
*B06B 1/02*    (2006.01)
*G01S 7/52*    (2006.01)
(Continued)

(52) U.S. Cl.
CPC .............. *A61B 8/56* (2013.01); *A61B 8/4444* (2013.01); *B06B 1/0215* (2013.01);
(Continued)

(58) Field of Classification Search
CPC ....... A61B 8/4444; A61B 8/56; A61B 8/5223; B06B 1/0215; B06B 1/0246;
(Continued)

(56) References Cited

U.S. PATENT DOCUMENTS 7,252,004 B2 *  8/2007  Fink ................... G01S 15/8915
                                                            73/597
7,891,230 B2 *  2/2011  Randall ................... A61B 8/00
                                                            73/1.82
(Continued)

FOREIGN PATENT DOCUMENTS

EP    1353195 A1    10/2003
EP    1445624 A2    8/2004
(Continued)

*Primary Examiner* — Jacques M Saint Surin (57) ABSTRACT

The high voltage drive for the transducer of an ultrasonic transducer probe is provided by an active supply that monitors the high voltage supplied to the transducer by means of feedback, and responds to a decline in voltage during high voltage transmission by coupling charge from a capacitor to the high voltage supply line of the probe, thereby preventing a precipitous decline in the high voltage. Preferably the active supply and the capacitor are located in the probe connector enclosure.

15 Claims, 7 Drawing Sheets

(51) Int. Cl.
  *G01S 15/89*   (2006.01)
  *A61B 8/00*   (2006.01)
  *A61B 8/08*   (2006.01)
(52) U.S. Cl.
  CPC .......... *B06B 1/0246* (2013.01); *G01S 7/5202* (2013.01); *G01S 7/52096* (2013.01); *G01S 15/8915* (2013.01); *A61B 8/5223* (2013.01); *B06B 2201/76* (2013.01)
(58) Field of Classification Search
  CPC ............... B06B 2201/76; G01S 7/5202; G01S 15/8915; G01S 7/52096
  USPC .......................................................... 73/596
  See application file for complete search history.

(56) References Cited

U.S. PATENT DOCUMENTS

| | | | | |
|---|---|---|---|---|
| 2007/0239019 A1* | 10/2007 | Richard | ................... | A61B 8/00 600/459 |
| 2008/0122407 A1 | 5/2008 | Khashayer | | |
| 2008/0194963 A1* | 8/2008 | Randall | ................... | A61B 8/00 600/459 |
| 2008/0194964 A1* | 8/2008 | Randall | ................... | A61B 8/00 600/459 |
| 2008/0214938 A1* | 9/2008 | Solomon | ................... | A61B 8/00 600/459 |
| 2012/0078112 A1* | 3/2012 | Asafusa | ............... | G01S 7/52017 600/459 |
| 2014/0018668 A1* | 1/2014 | Zheng | ................... | A61B 8/4254 600/424 |
| 2015/0018678 A1* | 1/2015 | Komuro | ................... | A61B 8/12 600/437 |
| 2015/0182201 A1 | 7/2015 | Steinbacher et al. | | |
| 2016/0081665 A1* | 3/2016 | Park | ................... | A61B 8/5269 600/443 |
| 2017/0176581 A1* | 6/2017 | Ku | ........................ | A61B 8/145 |

FOREIGN PATENT DOCUMENTS

| | | | |
|---|---|---|---|
| EP | 2711092 A1 | | 3/2014 |
| WO | 2013179179 A2 | | 12/2013 |
| WO | WO2017095010 | * | 6/2017 |

* cited by examiner

ACTIVE DISTRIBUTION OF HIGH-VOLTAGE POWER FOR ULTRASOUND TRANSDUCERS

This application is the U.S. National Phase application under 35 U.S.C. § 371 of International Application No. PCT/IB2016/056582, filed on Nov. 2, 2016, which claims the benefit of Provisional Application Ser. No. 62/249,416, filed Nov. 2, 2015. These applications are hereby incorporated by reference herein.

This invention relates to medical diagnostic ultrasonic imaging and, in particular, to powering ultrasonic transducer probes.

Ultrasound transducer probes, such as those used for 3D imaging, can have transmit circuitry located in the probe and coupled to the transducer array (sensor,) which excites the transducer elements with energy from power supplies located in ultrasound system. For some imaging modalities, such as shear-wave elastography or PW Doppler, and for probes used for therapeutic applications, the front-end circuitry can require higher electrical currents than the system power supplies are capable of supplying. An attempt by a probe to draw these high currents can result in a decline of the voltage level of the high-voltage supply which provides drive voltage to the front-end and the transducer, which in turn results in a drop in the acoustic pressure of the transmitted ultrasound, which degrades imaging and therapeutic effect. One approach to compensating for this problem is a passive approach, which is to couple a large capacitance to the high voltage supply line. International patent publication WO 2013/179179 describes the use of a large capacitor bank (100 µF to >1000 µF) coupled to the probe's high voltage supply line and located in either the ultrasound system mainframe, the transducer's system connector, and/or in the probe case. When the probe begins to draw excessive current during a transmit phase, the charge stored in the capacitor bank supplements that from the power supply, maintaining the desired voltage level.

This approach is not without its drawbacks, however, which involve the placement of a physically sizeable capacitor bank. When it is desired to locate the capacitor bank in the probe itself, the amount of space available is limited for ergonomic reasons and possibly also the probe's application, e.g., a TEE probe which needs to fit in the esophagus. When it is desired to locate the capacitor bank in the transducer's connector, the physical size of the capacitor bank is better accommodated, but the electrical resistance of the transducer cable becomes a constraining factor. For example, if the imaging modality can tolerate a 1 volt decline during a transmit pulse that requires 5 A, the cable resistance needs to be less than 0.2Ω. If a typical two-meter long cable for a 3D transducer probe distributes transmit power through a pair of conductors with a resistance of 2 ohms, the voltage drop caused by the cable is ten times that of an acceptable decline. This could be overcome by increasing the number of or diameter of the cable conductors, but this would make the cable less flexible, more expensive, and require the development of a new cable. It can also increase the size of the wire connectors at the ends of the cable. Accordingly it is desirable to solve the high-current voltage drop problem without compromising other aspects of the ultrasound system and probe.

In some aspects, the present invention includes ultrasound imaging systems including an active supply provides power to the array transducer in an ultrasound probe. For example, the ultrasound imaging systems can include an ultrasonic transducer located in a probe enclosure, an active supply, having an input coupled to a high voltage supply and an output coupled to the ultrasonic transducer, and a voltage feedback line coupled between the ultrasonic transducer and the active supply. The active supply can be configured to adjust an output voltage supplied to the ultrasonic transducer based on a feedback voltage from the voltage feedback line.

In certain aspects, the active supply, which supplies energy to the probe through conductors in the transducer cable, may be located a various places in the imaging system, such as in an ultrasound system mainframe, the transducer probe itself, or in the transducer probe's connector.

In some aspects, the active high voltage supply can be coupled to a capacitor bank, which is charged to a higher voltage. The capacitor bank can discharge by tens of volts during operation, but the active supply maintains the voltage at the transducer front end within a higher range that is acceptable for imaging. The active supply receives feedback from a point closer to the sensor in the signal path and an error amplifier compares the feedback signal to a reference either generated on the connector or provided by the ultrasound system. In response to the error amplifier output, the active supply changes its output to compensate for the change in the load presented by the front end sensor. The capacitor bank stores enough charge for the active supply to provide the current needed by the sensor throughout the duration of the transmit excitation. The voltage of the capacitor bank can be high enough for the active supply to maintain the desired voltage at the transducer through the transmit interval. The use of the active supply allows use of the capacitor bank on the order of hundreds of microfarads instead of thousands as in the passive case, because its voltage decline can be many more volts than the voltage at the transducer front-end.

Figure 1:
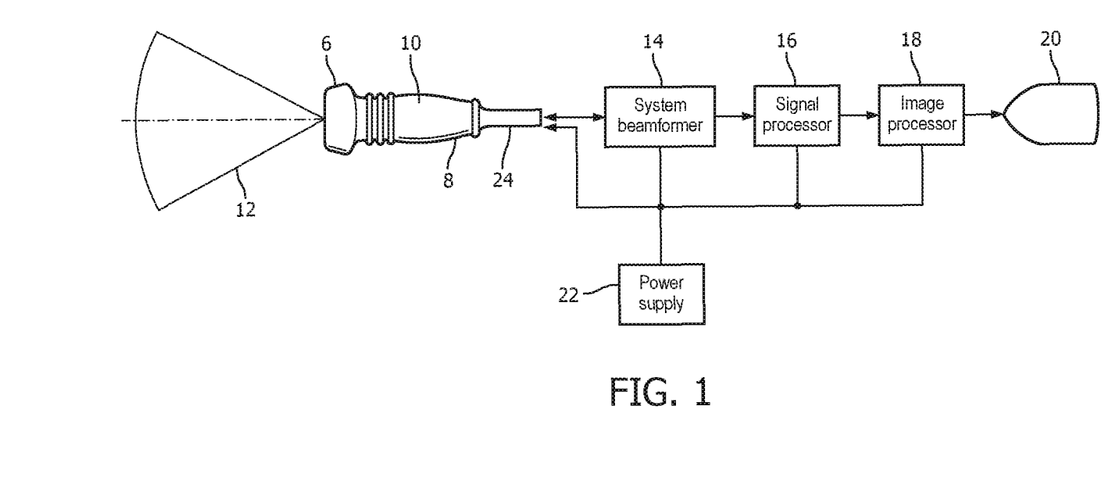
FIG. 1 is a schematic diagram of an ultrasound system constructed in accordance with the principles of the present invention.

Referring first to FIG. 1, an ultrasound imaging system constructed in accordance with the principles of the present invention is shown in block diagram form. An ultrasound probe enclosure 10 is provided which is to be held by its handle section 8 with its distal end 6 against the body of a patient to image the anatomy below the point of contact. An array transducer inside the distal end 6 of the probe enclosure transmits focused pulses or waves along directions referred to as beam directions over a two or three dimensional region of the body. This region is shown as a sector-shaped plane 12 in FIG. 1. Transmission is accomplished by applying high voltage pulses or waveforms to elements of the array transducer by transmitters located in the probe or an ultrasound system mainframe, to which the probe can be connected by a cable 24 or wirelessly. Echoes are returned from tissue, blood and structures along the beam directions in response to each transmission and the echoes are processed by beamforming with a system beamformer 14 to form coherent echo signals from the ultrasound signals received by elements of the array transducer. Some or all of the beamforming may also be performed by a microbeamformer ASIC located in the probe and coupled to the array transducer. After the received signals have been fully beamformed they are coupled to a signal processor 16 which performs functions such as decimation, filtering, harmonic separation, and signal compounding. The processed signals are coupled to an image processor 18 which forms them into images by processes such as amplitude or Doppler detection and scan conversion. The formed images are displayed on an image display 20.

The system includes a power supply 22 which provides a number of voltages used to energize the various components of the ultrasound system. The power supply 22 can be coupled to an active supply 40 as described further herein and can provide a high voltage (e.g., ~100v) for use by the transmitter circuits to stimulate the transducer elements to transmit pulses or waves for imaging or therapy. The high voltage can be applied to transmitters in the system mainframe and/or transmitters in the probe 10.

Figure 2:
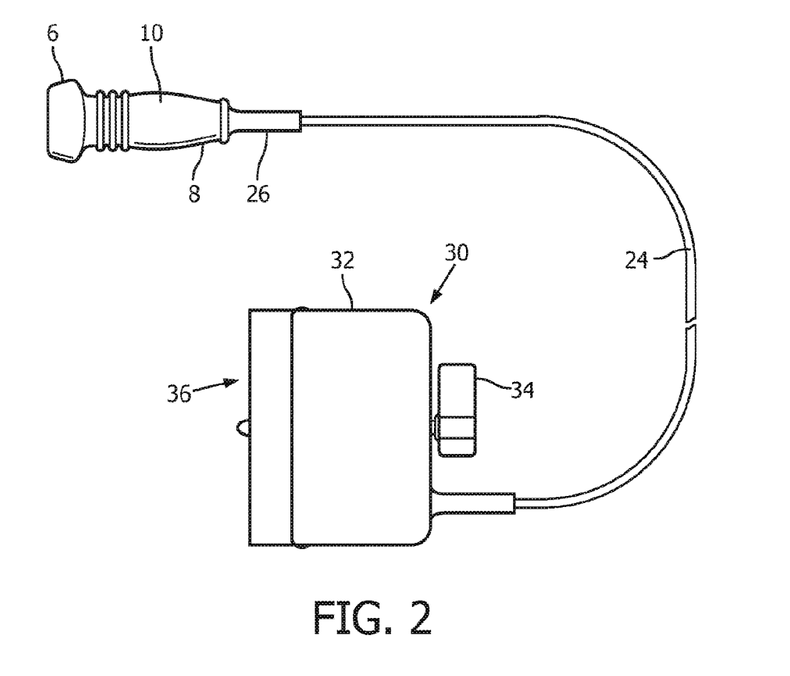
FIG. 2 illustrates a probe with its cable and connector for an ultrasound system mainframe.

In some aspects, an ultrasound system mainframe is included in the system and is operable with a number of different types of probes for different diagnostic applications. For this purpose the system mainframe can include one or more connectors to which probes may be connected. FIG. 2 illustrates a probe 10 with a connector 30 at the proximal end of the cable 24. Strain reliefs 26 prevent excessive flexing at the ends of the cable where it is attached to the probe and probe connector. The probe connector 30 comprises a case which contains a multi-pin plug to which the conductors of the cable are connected. The plug is indicated at 36. To attach the probe to the system mainframe, the plug 36 is plugged into a mating connector on the ultrasound system and a lock handle 34 is turned to securely attach it to the system.

Figure 3A:
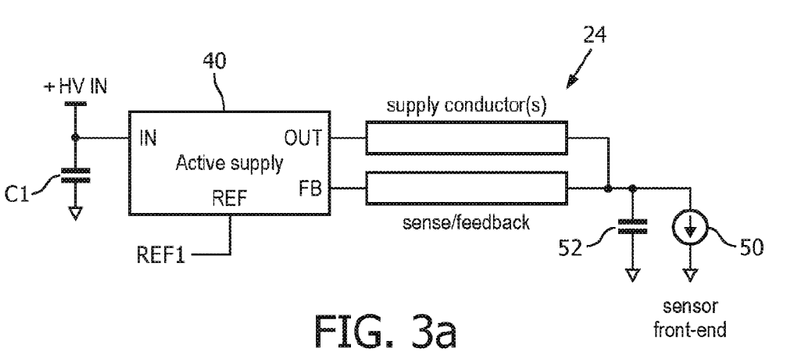
FIGS. 3a and 3b illustrate schematic implementations of the present invention for positive and negative supply voltages.
Figure 3B:
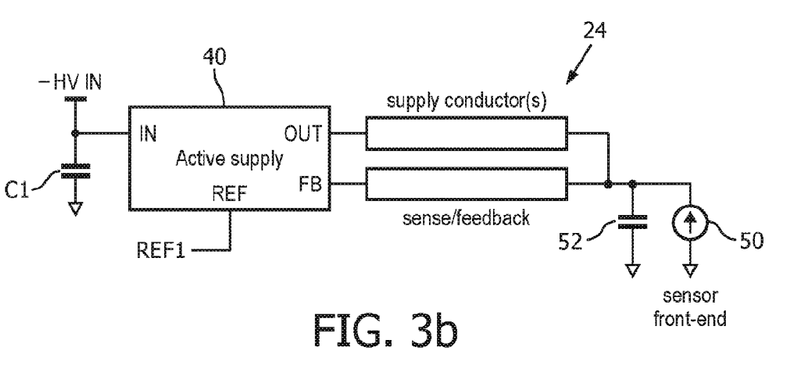

As previously mentioned, the demands on the high voltage supply when driving the transducer elements in some applications can cause the voltage to be drawn down during high transmit current demands. The decline in the supply voltage will provide a lower than desired voltage level at the probe sensor, which in turn will produce transmit signals of less than the desired acoustic pressure. The use of capacitor banks to supplement the high voltage supply during these transmit intervals faces the limitations described above. In accordance with the principles of the present invention, an active supply 40 is used to provide a high voltage to the sensor as illustrated in FIGS. 3a and 3b. An active approach for supplying transmit energy can achieve the same supply voltage performance as the passive capacitor bank approach, but with less capacitance (e.g., about 90% less capacitance) and, as a result, a much smaller space requirement in the probe or system. Thus, an active supply and its capacitance can readily fit in several parts of an ultrasound system, including the probe, the system mainframe, and most conventional probe connectors. Furthermore, the active approach can use existing transducer cable designs. FIG. 3a shows a simplified block diagram of an active supply for a transmitter in a transducer probe 10. In this implementation the active supply 40 is located in the transducer connector 30 and supplies energy through conductors in the transducer cable 24. The active high voltage supply 40 is powered by a high voltage (+HV IN) from the power supply 22, which is applied to a capacitor C1 at the input of the active supply. The power supply charges the capacitor C1 to the high supply voltage. The capacitor C1 can discharge by tens of volts during operation, but the active supply maintains the voltage at the probe's front end sensor 50 within a tighter range that is acceptable for imaging and therapy. The active supply receives feedback from the sensor along a voltage feedback line, and compares the feedback voltage in the circuitry to a reference voltage either generated in the connector 30 or provided by the ultrasound system mainframe. One example of how the active supply compares the feedback voltage is explained with respect to the circuit in FIG. 5 below. In response to a change in the feedback signal, the active supply varies its output to compensate for the change in the load presented by the sensor. The capacitor C1 stores enough charge for the active supply 40 to provide the current needed by the sensor 50 and its bypass capacitance 52 for the duration of the transmit excitation period. The voltage at the capacitor C1 only needs to be high enough for the active supply to maintain the voltage at the sensor through the transmit interval. The capacitor C1 can be on the order of hundreds of microfarads instead of thousands as in the passive case, because it can drop by many more volts than the actively controlled voltage at the sensor front-end.

It should be noted that the active supply can provide either a positive or a negative high voltage and that the sensor load can source or sink current.

A sensor (e.g., a voltage sensing device) may utilize one or both polarities of high voltage. FIG. 3b schematically illustrates the same arrangement as FIG. 3a but for a sensor requiring a negative (−HV) drive voltage. A negative high voltage is applied to the capacitor C1 at the input to the active supply 40, and the current flow is in the opposite sense as indicated by the direction of the arrow in the symbol for the sensor 50.

Figure 4:
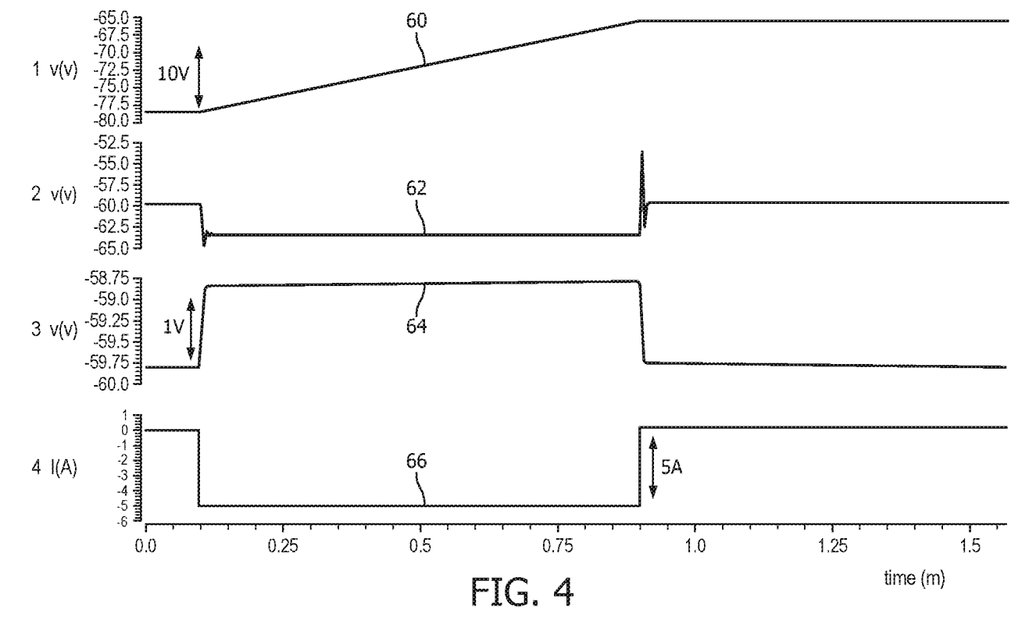
FIG. 4 illustrates voltage and current levels during a transmit pulse at different points in an implementation of the present invention.

FIG. 4 illustrates exemplary waveforms at points in the circuit of FIG. 3b during the supply of a high negative transmit voltage. In this example the input to the active supply 40 is −77V, the voltage at the sensor 50 is maintained to within 1V of −60V during a transmit interval of less than one millisecond, during which 5 amps (A) is drawn by the sensor. The capacitor C1 has a value of 300 μF and the voltage at the input to the active supply drops by 10V, from −77V to −67V as shown by curve 60. Negative feedback from the sense conductor of the cable 24 forces the active supply 40 to decrease the voltage at the connector end of the supply conductor of the cable 24 to compensate for the voltage drop over the cable when the sensor sinks 5 A into the cable. This is shown by curve 62, where the nominal −60V is changed to −62.5V to account for the cable's voltage drop. Curve 64 shows the voltage change at the sensor, which is from −60V to −59V, an acceptable one volt decline, which occurs when the sensor is drawing 5 A as shown by curve 66. The capability of sinking 5 A at −60V during the transmit interval is something that the typical ultrasound system power supply cannot do with this performance.

Figure 5:
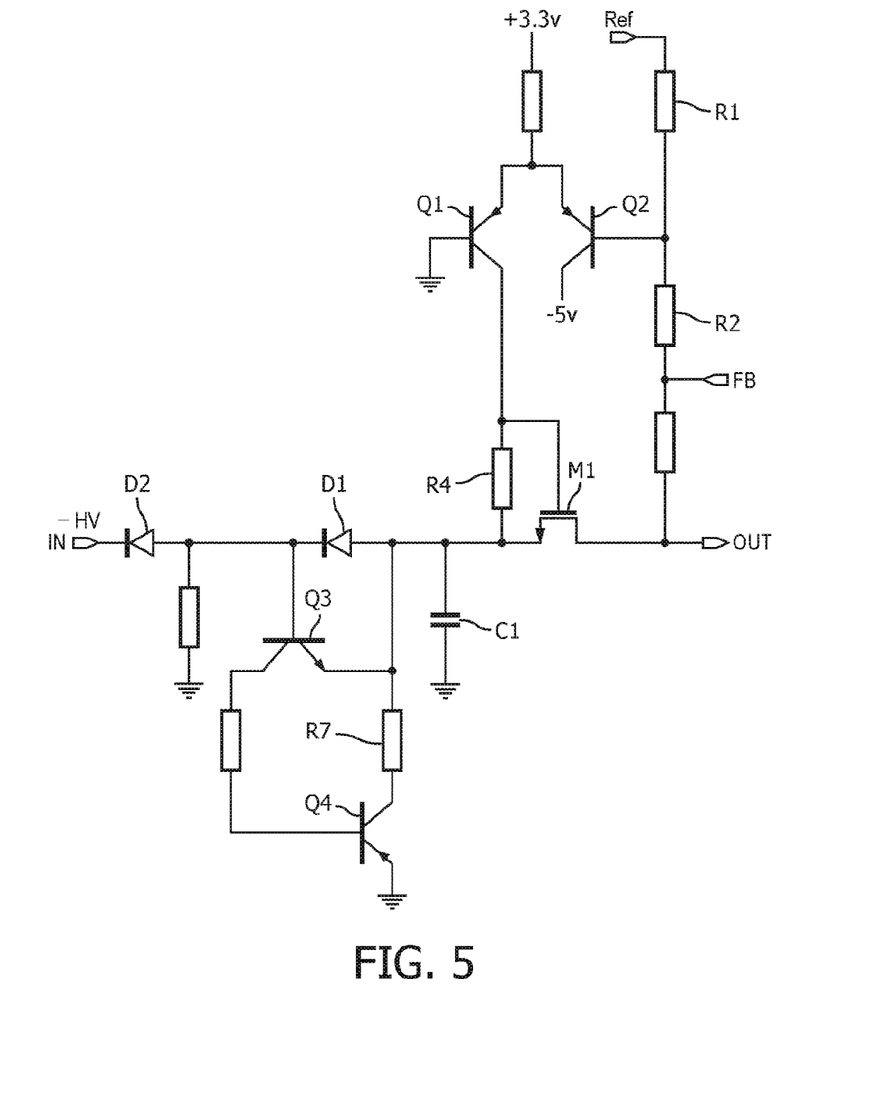
FIG. 5 is a schematic diagram of an active supply constructed in accordance with the principles of the present invention.

An exemplary schematic for an active supply of the present invention having the performance illustrated in FIG. 4 is shown in FIG. 5. The active supply in this example is implemented as a high voltage linear regulator. It will be understood that switching supplies can also be used. The linear regulator as shown receives negative feedback from the sensor 50 at terminal FB, which enables it to maintain an approximately constant voltage at the feedback point, as the load and its input voltage vary. Since the high voltage supply −HV coupled to the input terminal IN of the linear regulator cannot sink 5 A, the negative voltage on the capacitor CI will rise towards 0V during the load (transmit) interval.

The regulator compensates for the change in load and its input voltage variation by varying the drain to source resistance of its NMOS pass transistor M1. A feedback network consisting of resistors R1 and R2 sets the voltage to be produced for the supply conductor(s) at the output terminal OUT to be approximately equal to a reference voltage Ref. supplied by the ultrasound system, multiplied by −1. Transistors Q1 and Q2 form an operational transconductance amplifier. The current output of Q1 drives the gate of the pass transistor M1 to a voltage which is set by resistor R4, thereby controlling the resistance between the input voltage to the regulator and the supply conductor(s). If the amount of current that the load sinks into the supply increases, the voltage at the regulator output increases, which decreases the base-emitter voltage of transistor Q2. This causes the collector-emitter current of transistor Q2 to decrease and collector-emitter current of transistor Q1 to increase, which raises the gate-source voltage of pass transistor M1. The increased gate-source voltage lowers the drain-source resistance of pass transistor M1, which is in series with the input supply to the regulator and its output, resulting in a lower output voltage.

Similarly, if the sensor load decreases, the voltage at the regulator output will decrease, which increases the bias of Q2 and results in an increase in the conductivity of Q2 and a decrease in the conductivity of Q1. This decreases the gate drive of the pass transistor, which raises its drain-source resistance and increases the output voltage of the regulator. The same mechanism causes the drain-source resistance of the pass transistor M1 to decrease as the input voltage to the regulator decreases; and increase as the input voltage increases when the high voltage system recharges the capacitor C1. Hence, the linear regulator holds the voltage at a set voltage as the load and its input voltage vary.

There is a discharge circuit in series with the ultrasound system and the linear regulator. The discharge circuit protects the ultrasound system from being back-driven by capacitor C1 when the negative high voltage supply is raised towards 0v. The discharge circuit also prevents a shock hazard which could occur if the capacitor C1 were directly connected to the probe connector 36. Diodes D1 and D2 become reverse-biased when −HV is increased by the system, or disconnected. The Q3 transistor then develops a positive bias on its base and drives the base of transistor Q4, which causes Q4 to discharge the capacitor C1 through R7 and transistor Q4.

Figure 6:
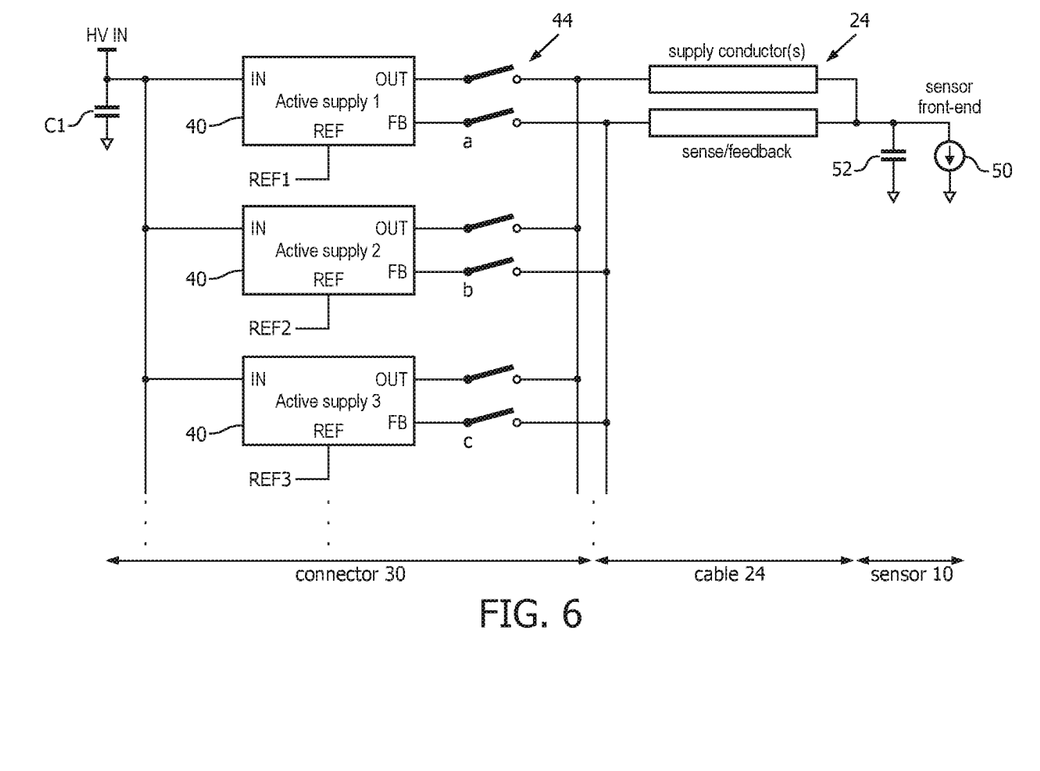
FIG. 6 is a block diagram of the supply of probe power using multiple active supplies.
Figure 7:
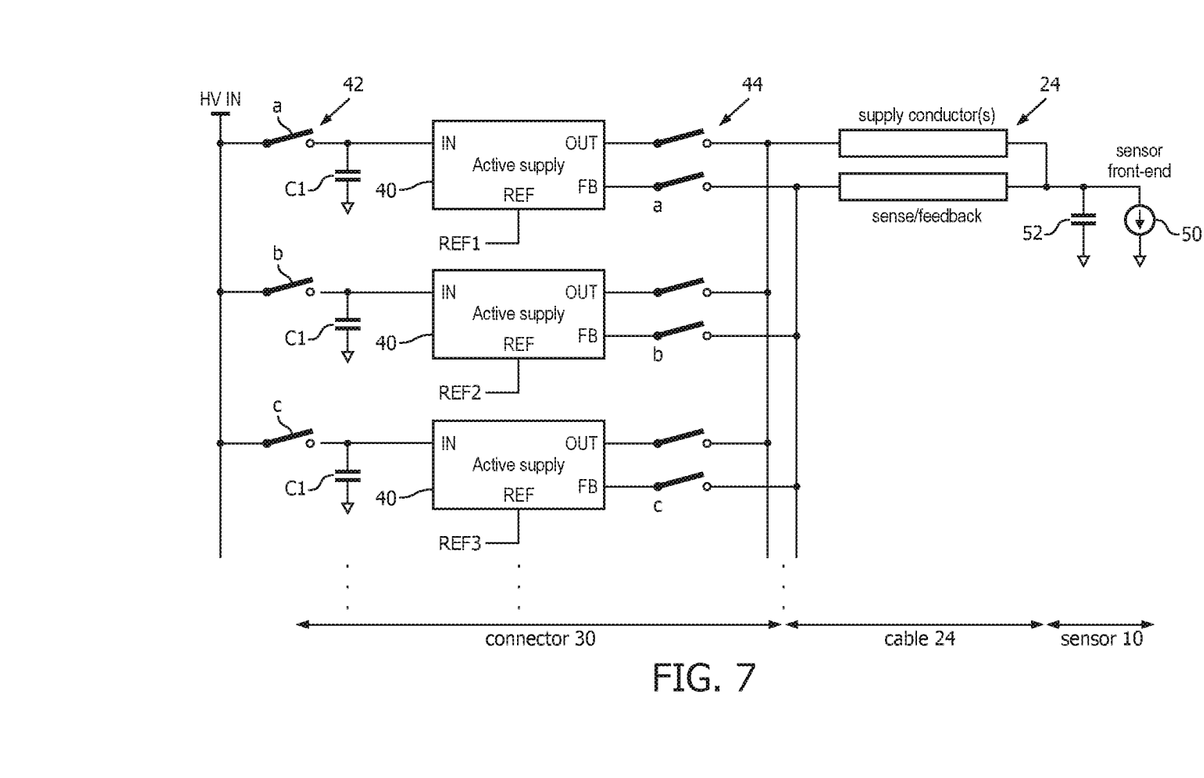
FIG. 7 is a block diagram of another implementation of the supply of probe power using multiple active supplies.

In order to image with transducer excitations of different voltages, an implementation of the present invention can employ multiple active supplies 40 and switches 44a, b, and c to change the actively controlled high voltages for the transducer when the excitation voltage changes. This is illustrated in FIG. 6. The illustrated switching arrangement switches both the supply conductor and the sense line connections. The active supplies 40 are shown with a single capacitor C1. FIG. 7 shows the same multiple excitation voltage implementation, but with different charge storage capacitors C1 for the different active supplies 40. Switches 42a, b and c selectively couple the system high voltage HV to the capacitors C1.

What is claimed is:

1. An ultrasound imaging system, comprising:
    an ultrasonic transducer located in a probe enclosure;
    an active supply, comprising:
        a linear regulator;
        an input coupled to a high voltage supply; and
        an output coupled to the ultrasonic transducer; and
    a voltage feedback line coupled between the ultrasonic transducer and the active supply,
    wherein the linear regulator is configured to maintain an output voltage supplied to the ultrasonic transducer during a transition from a first ultrasound modality at a first electrical load to a second ultrasound modality at a second electrical load based on a feedback voltage from the voltage feedback line.

2. The ultrasound imaging system of claim 1, comprising a capacitor coupled to the input of the active supply.

3. The ultrasound imaging system of claim 2, comprising a reference voltage source coupled to the active supply.

4. The ultrasound imaging system of claim 2, comprising a probe connector coupled to an end of a probe cable coupled to the probe enclosure,
    wherein the active supply is located in the probe connector.

5. The ultrasound imaging system of claim 4, wherein the capacitor is located in the probe connector.

6. The ultrasound imaging system of claim 5, wherein the probe cable comprises a high voltage supply conductor coupled between the active supply and the ultrasonic transducer, wherein the voltage feedback line is located in the probe cable, and wherein the high voltage supply is located in an ultrasound system mainframe.

7. The ultrasound imaging system of claim 1, wherein the active supply comprises an operational transconductance amplifier configured to adjust the output voltage supplied to the ultrasonic transducer based on the feedback voltage from the voltage feedback line.

8. The ultrasound imaging system of claim 7, comprising a pass transistor configured to control conduction between the capacitor and the active supply output.

9. The ultrasound imaging system of claim 1, comprising a transmitter coupled to the ultrasonic transducer,
    wherein the active supply is coupled to provide high voltage to the transmitter.

10. The ultrasound imaging system of claim 2, wherein the active supply is located in the probe enclosure.

11. The ultrasound imaging system of claim 2, wherein the active supply is located in an ultrasound system mainframe.

12. The ultrasound imaging system of claim 11, wherein the active supply further comprises a discharge circuit, coupled to the capacitor, to discharge the capacitor when the probe is disconnected from the system mainframe.

13. The ultrasound imaging system of claim 1, wherein the active supply is configured to output a first high voltage to the ultrasonic transducer; and the system further comprises:
    a second active supply having an input coupled to the high voltage supply and an output coupled to the ultrasonic transducer such that the active supply is configured to provide a second high voltage to the ultrasonic transducer.

14. The ultrasound imaging system of claim 13, further comprising a switch coupled between the high voltage supply and the input to each active supply.

15. The ultrasound imaging system of claim 13, further comprising a switch located between the output of each active supply and the ultrasonic transducer, and a switch located between a feedback input of each active supply and the ultrasonic transducer.

* * * * *